United States Patent [19]

Dulin

[11] Patent Number: 5,221,506
[45] Date of Patent: Jun. 22, 1993

[54] BAR SOAP WITH STRUCTURAL CORE

[76] Inventor: Jacques M. Dulin, 16310 Jackson Oaks Dr., Morgan Hill, Calif. 95037

[21] Appl. No.: 464,296

[22] Filed: Jan. 12, 1990

[51] Int. Cl.⁵ .............................................. C11D 11/00
[52] U.S. Cl. ........................................ 252/92; 252/91; 252/93; 252/DIG. 5; 252/DIG. 16
[58] Field of Search .................. 252/92, 93, DIG. 16, 252/DIG. 5, 91

[56] References Cited

U.S. PATENT DOCUMENTS

| | | | |
|---|---|---|---|
| 1,748,406 | 2/1930 | Blair | 401/201 |
| 2,588,773 | 3/1952 | Smith | 401/201 |
| 3,114,928 | 12/1963 | Spiteri | 401/201 |
| 3,293,684 | 12/1966 | Tundermann | 252/92 |
| 3,773,672 | 11/1973 | Bredice | 252/92 |
| 3,931,035 | 1/1976 | Brown | 252/93 |
| 3,949,137 | 4/1976 | Akrongold et al. | 252/92 |
| 4,240,760 | 12/1980 | Levine | 252/92 |
| 4,308,157 | 12/1981 | Di Giovanna | 252/93 |
| 4,311,604 | 1/1982 | Hörnig | 252/90 |
| 4,438,010 | 3/1984 | Lindauer et al. | 252/91 |
| 4,457,643 | 7/1984 | Caniglia | 401/201 |
| 4,613,446 | 9/1986 | Magyar . | |
| 4,741,852 | 5/1988 | Ondracek | 252/92 |
| 4,746,454 | 5/1988 | Iknadossian | 252/170 |

FOREIGN PATENT DOCUMENTS

| | | | |
|---|---|---|---|
| 1956993 | 5/1971 | Fed. Rep. of Germany | 252/92 |
| 3329305 | 2/1987 | Fed. Rep. of Germany | 252/92 |
| 62-48799 | 8/1985 | Japan | 252/92 |
| 7905285 | 1/1981 | Netherlands | 252/92 |
| 2192639 | 1/1988 | United Kingdom | 252/92 |

*Primary Examiner*—Prince Willis, Jr.
*Assistant Examiner*—J. Silbermann
*Attorney, Agent, or Firm*—Rosenblum, Parish & Isaacs

[57] ABSTRACT

Bar soap for personal use having a structural center selected from an open celled sponge material, or woven or non-woven organic filamentary material, which is preferably fully soap-impregnated. The sponge core is revealed after the soap bar is reduced to a sliver, providing support, preventing breakage and making washing more effective and reducing wastage. Water soluble oxycellulose polymers may be used. The sponge may be configured in the form of a character or animal shape for children. The core may extend to at least one surface and can be configured to provide a hanger support. The core permits dipping to build up the bar, and layered soap of different compositions or colors is disclosed.

14 Claims, 1 Drawing Sheet

BAR SOAP WITH STRUCTURAL CORE

FIELD

This application relates to bar soap, more particularly to an improved bar soap having a structured center which preferably is a sponge, fully soap-impregnated. The sponge provides structure when the soap bar is reduced to a sliver, making washing more effective and reducing wastage.

BACKGROUND AND INFORMATION DISCLOSURE STATEMENT

Soap in bar or cake form is conventional and has been in use over a hundred years. However, as it is used it becomes reduced to a sliver which breaks up easily. Typically, slivers are wasted, turning to jelly in soap dishes, crumbling and being flushed away in use, or being thrown away.

Another problem with bar-form soap is that people wash incorrectly with it. They wash with the bar, rubbing their skin with the bar. They should rub the wet bar on a wet washcloth and wash with the soapy cloth. TV and print media ads show washing with the bar itself, encouraging misuse. The use of the bar itself to wash is such a habit that when the bar is reduced to a sliver it becomes so hard to wash in that manner that the tendency to throw the sliver 5 away is encouraged. Further, it is hard to soap-up a washcloth when the bar is a sliver. A dropped sliver breaks easily, especially the feather edges. All these problems encourage waste and inefficient washing as the bar-on-skin wash method does not give adequate washing contact.

The prior art does not address or solve these problems. Some soap bars for shower use employ ropes embedded in them to assist in retrieving them when they drop. The rope usually breaks out when the bar is reduced in size.

The other common approach puts the soap bar inside a sponge, not vice versa. Blair U.S. Pat. No. 1,748,406 provides a large sponge with a center pocket and a curved openable flap in one side face for inserting the bar of soap. Putting the bar inside the large sponge pocket is said to provide a constant supply of soap lather to the sponge. Smith U.S. Pat. No. 2,588,773 also puts a bar of soap in a sponge pocket, provides snap-closeable access at one end, and channels in one face to permit water access and lather exit. Spiteri U.S. Pat. No. 3,114,928 provides a pocket in a sponge with the end opening closeable by Velcro TM material. Caniglia U.S. Pat. No. 4,457,643 provides a sponge having a center pocket for a bar of soap, curved sides for entry end. Iknadosssian U.S. Pat. No. 4,746,456 provides a cleaning composition including potato pulp. It does not appear relevant but may be the shortest U.S. patent.

Brillo TM-type soap pads are largely kitchen scrubbers made of metal or tough plastic that are partly impregnated with slow dissolving, high strength soap which includes abrasive agents. At most the soap is a small core, the purpose being to present a non-woven, tough scrubbing surface to remove baked-on or dried food and food stains from dishes, pots and pans, and counter surfaces. They are not used as bath or cosmetic soap bars. Lava TM-type soap bars contain pumice uniformly throughout to provide abrasive cleaning action.

There is thus a need for better and complete use of bar soap that overcomes the problems noted.

THE INVENTION

Objects

It is a principal object of the invention to solve the bar soap wasted sliver problems noted.

Other objects will be evident from the specification and drawings.

Summary

The invention comprises a sponge core in a soap bar. It is preferred that the sponge be open celled, that the cells be large and exposed, and that the sponge be fully impregnated with soap to provide a structurally supported core, herein termed a "structured bar soap". While a core comprising from about 5% to 50% of the volume of the soap bar is preferred, permitting the sponge structured support to extend outwardly to, or to near the surface is also part of the invention. While the preferred structural support is a natural or synthetic open-celled sponge material, any oriented, woven or non-woven material of suitable abradable qualities and strength may be employed. For example, heavy duty cleaning (shop soap) bars may use relatively tougher structural materials alone or in combination with conventional abrasives (pumice, diatomaceous earth, and the like materials) or conventional solvent-type cleaning compounds. In contrast, cosmetic soaps may employ light weight, very fine pore, easily abradable, open cell urethane foam. The soaps may be any conventional bath, hand and cosmetic soap, ranging from mild soap (e.g. Ivory TM brand), to deodorant general purpose soap (e.g., Dial TM or Irish Spring TM brands), to cosmetic soap (e.g. Camay TM, or Dove TM brands), and to heavy duty hand soaps (e.g., Lava TM brand).

As the soap bar is used down to the sliver size, the sponge supports the remaining core, permitting ease of use and reducing breaking. The washcloth can be eliminated as the ribs of the sponges cells or other structural member appearing in the revealed surface provide the appropriate texture for good cleaning, assisting in removing dead skin cells, cleaning pores, dirt, stains, etc. Once the soap is completely used, the consumer has a reusable general purpose or special purpose sponge.

In one embodiment the sponge is configured, e.g. in a dinosaur or cartoon character shape, to encourage children to use the soap. The revealed shaped sponge is a surprise to the child that rewards washing. Different bars can contain different figures or parts of an animal or figure. The parts or figures may be collected and assembled as a premium item. Also the remaining sponge core provides the user with a positive feeling there is something of value left; not all of it has gone down the drain.

The structured soap bars of this invention can be made in a variety of ways. Preferably the sponge is first impregnated to its surface or near thereto, with liquid soap, let dry, and then (if the bar is cast hot or warm), the impregnated sponge core is put in place (e.g. when the bar is half cast) and the remainder of the bar cast therearound and cooled.

Alternately, the dried core may be repeatedly dipped to complete the bar. This dipping procedure can provide a bar of layered colors, or alternately, different types of soap, e.g. abrasive soap alternating with milder soap for shop use. The outer abrasive layer is used initially to remove heavy grime and grease, while the subsequent (next inner layer) conditions the skin. When the next abrasive layer is revealed (by texture or color) it is a signal to stop use at that washing or for that area.

In another method of constructing the structured soap bar of this invention, a highly viscous water solution of soap (liquid soap) is poured into the mold to approximately one-third the depth of the mold (which represents the thickness of the bar), and let dry. A damp sponge core is then centered in the mold and additional viscous liquid soap is poured into the mold and let dry. In still another method, the mold is oriented with the bar length vertical. A damp sponge is centered in the middle with a support (fine wire or plastic filaments from the open top, or prongs from the mold sides in the case of a two-part or more separable mold). Liquid or warm (molten) soap is poured or cast therein and let dry or cool, as the case may be. Alternately, one or more tab portions of the sponge may extend above the mold top. When dry or cool, the supports are pulled out, or the filament or sponge tab trimmed at the bar surface. Where the soap is poured or cast in a large block and bars cut therefrom, the sponge may extend to one or more of the edges.

In another alternative, the soap bar structural support may be made of a water soluble polymer, preferably having a slower dissolution rate then the soap, for example, a conventional oxycellulose of suitable molecular weight. Thus, as the bar is used, the structure supports the core as described, is gradually revealed, and is abraded or dissolved away. As such, the core is biodegradable. Any other conventional biodegradable plastic may be used. The plastic used is preferably non-allergenic, such as polyolefin or plastics, pvc, pvp and the like.

DETAILED DESCRIPTION OF THE BEST MODE

The following detailed description illustrates the invention by way of example, not by way of limitation of the principles of the invention. This description will clearly enable one skilled in the art to make and use the invention, and describes several embodiments, adaptations, variations, alternatives and uses of the invention, including what I presently believe is the best mode of carrying out the invention.

Figure 1:
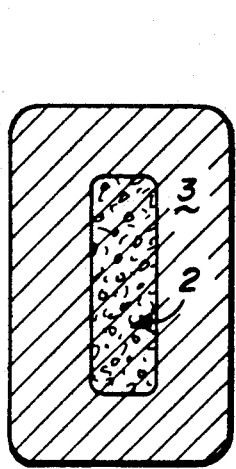
Figure 6:
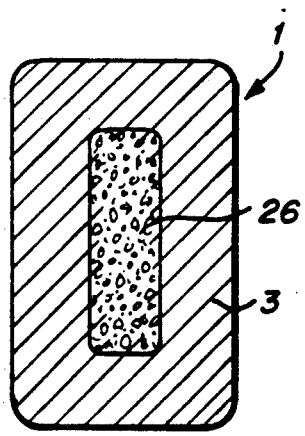

FIG. 1 shows a structured soap bar of this invention 1 having a soap-impregnated core 2 surrounded by soap 3. FIG. 6 shows an alternate embodiment in which the core 26, here a sponge, is not pre-impregnated with soap, so that the soap 3 (shown with the shaded lines) during manufacture only extends part way into the surface of the sponge core, as shown by the shading lines extending only partway into the sponge, sufficient to bind well to the sponge core.

Figure 2:
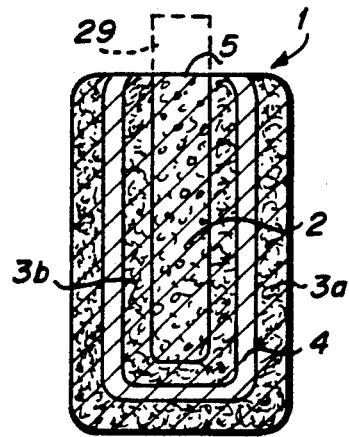

FIG. 2 shows a core 2 extending to at least one surface 5 where it is exposed. To manufacture the bar, a portion 2a of the core extends above the bar to engage suspension means (not shown). This portion 2a may be cut off at surface 5 if desired or left exposed and configured for a hanger support (e.g. a hole). FIG. 2 also shows a multi-layered bar, with the alternating layers 3a, 4 and 3b being of different color or composition. As shown in this example, layers 3a and 3b contain an abrasive such as pumice or diatomaceous earth, and layer 4 is a conditioning or antibacterial soap.

Figure 3:
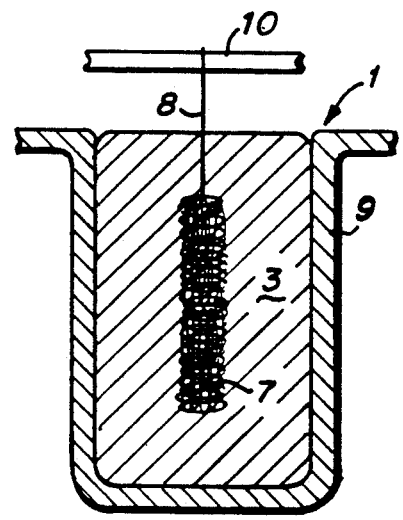

FIG. 3 shows a bar 1 in mold 9, having a non-woven or woven core 7 suspended by filament 8 from support 10. The filament is cut at surface 6 after the bar is solid.

Figure 4:
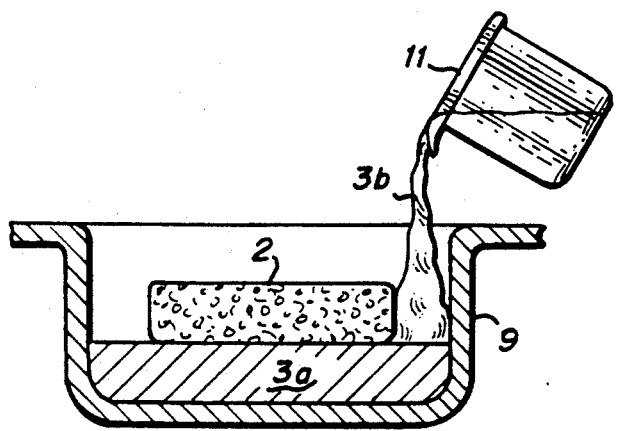

FIG. 4 shows a core 2 placed on a previously cast or formed soap surface 3a in mold 9, with additional same or different soap 3b being provided from container 11.

Figure 5:
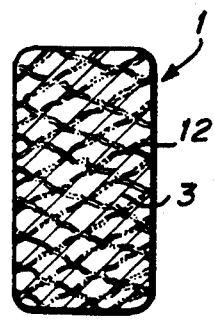

FIG. 5 shows a woven open lattice of soluble and/or biodegradable filaments 12 more uniformly supporting soap 3 in the structured soap bar 1.

It should be understood that various modifications within the scope of this invention can be made by one of ordinary skill in the art without departing from the spirit thereof. For example, the structure could be a lattice work of very hard soap impregnated with and surrounded by, to form the bar, a softer or more easily soluble solid soap. I therefore wish my invention to be defined by the scope of the appended claims as broadly as the prior art will permit, and in view of the specification if need be.

I claim:

1. Improved bar soap comprising in combination:
   a) a solid soap in a bar configuration, having an exterior surface, a first central zone, and a second zone intermediate with said first central zone and said surface;
   b) said solid bar is a personal use soap composition which is a member of group selected from a shop or lavatory hand soap, a deodorant soap, an antibacterial soap, a bath soap, a hair soap, a cosmetic soap and combinations thereof;
   c) a structural core disposed in at least said first central zone to provide physical support for said soap bar as it is reduced to a sliver upon use;
   d) said structural core is a member of a group selected from a sponge, a woven filamentary structure, a non-woven filamentary structure, an open lattice work of a second hard soap, and combinations thereof;
   e) said structural core comprises from 5 to 50% of the volume of said soap bar and is fully impregnated with said solid soap; and
   f) said solid soap forming said soap bar being more easily soluble than said second hard soap of said structural core.

2. Improved bar soap as in claim 1 wherein at least a part of said structural core extends to and is contiguous with the surface of said bar in new, finished condition.

3. Improved bar soap as in claim 1 wherein said structural core material is a member of a group selected from an abradable organic material, a water soluble material, and a biodegradable material.

4. Improved bar soap as in claim 3 wherein said core material is oxycellulose.

5. Improved bar soap as in claim 1 wherein at least a portion of said intermediate layer is selected from a soap of composition, color, or combinations thereof, different from other portions of said solid soap forming said bar.

6. Improved bar soap as in claim 5 wherein said intermediate layer different portion comprises at least one soap having abrasive material therein.

7. Improved bar soap as in claim 1 wherein said structural core is in the form of at least a part of a figure.

8. Improved bar soap as in claim 7 wherein said structural core figure is a part of a figure which is assembleage with other figure parts from other bar cores to form a completed figure.

9. Method of making a solid bar soap having an open structural core which supports the center of the soap bar preventing sliver breakage comprising the steps of:

a) providing a structural core which is a member of a group selected from a sponge, a woven filamentary structure, a non-woven filamentary structure, and open lattice work of a second hard soap, and combinations thereof;
b) providing fluid soap;
c) forming a zone of fluid soap in and around said core;
d) permitting said zone of fluid soap to harden into a first hard soap throughout said structural core to form a solid bar having an open structural core permeated with said first hardened soap, and said first hard soap is more easily soluble than said second hard soap of said core.

10. Method as in claim 9 wherein:
a) said core is supported in a bar soap mold; and
b) said fluid soap is cast around said core.

11. Method as in claim 10 wherein:
a) said structural core is fully impregnated with soap.

12. Method as in claim 10 wherein:
a) at least a portion of said core extends beyond one edge of said mold.

13. Method as in claim 9 wherein:
a) said core is dipped in said fluid soap.

14. Method as in claim 10 wherein:
a) at least two differing types or colors of liquid soap are provided;
b) repeating said dipping to build up layers of soap; and
c) said core is dipped at different times in said differing soaps to build up a soap bar with plural layers of different soaps.

* * * * *